Figure 1A:
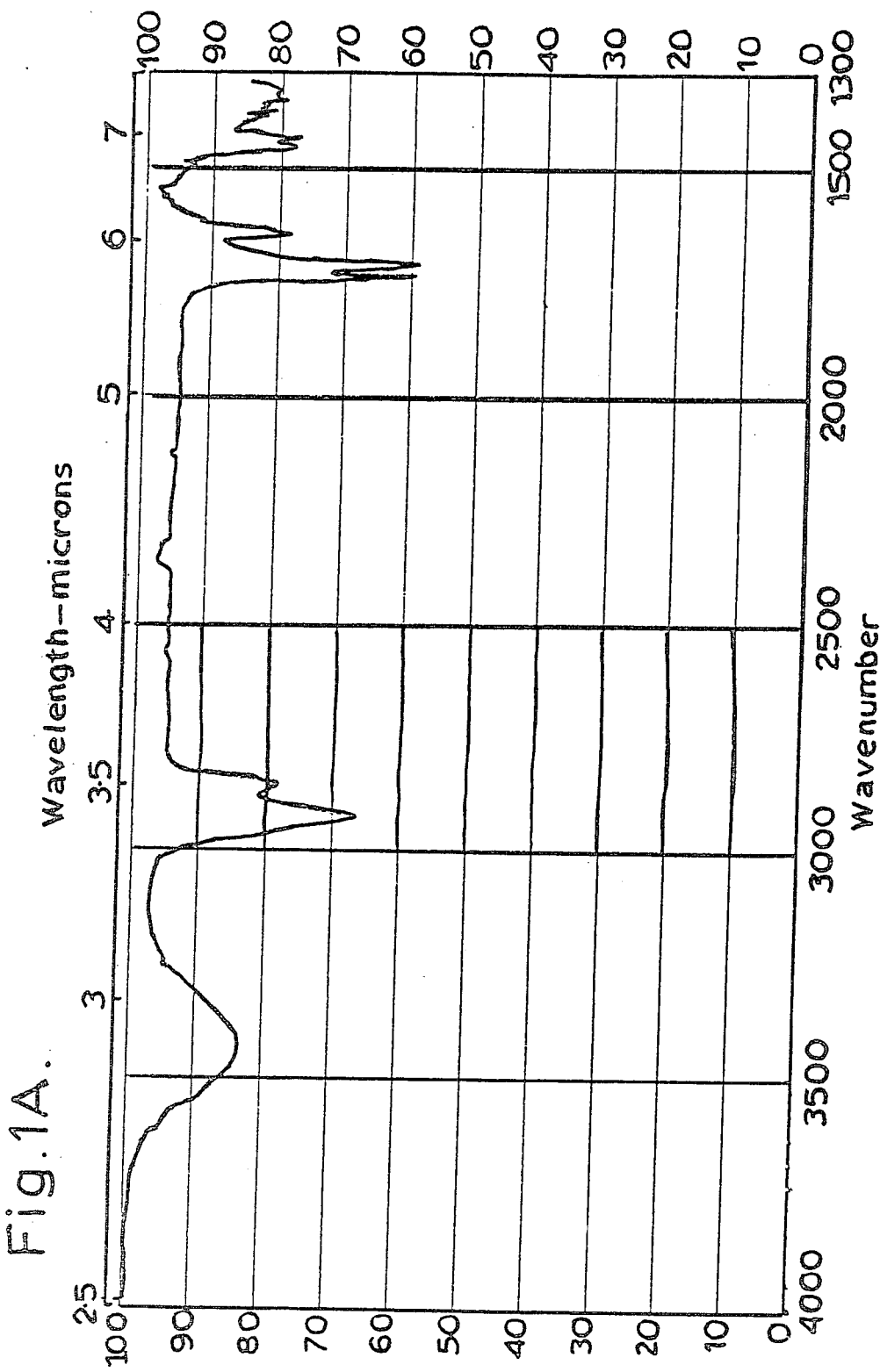

United States Patent [19]

Barrow et al.

[11] 4,289,703
[45] Sep. 15, 1981

[54] ANTIBIOTICS

[75] Inventors: Kevin D. Barrow, Kensington, Australia; Graham Mellows, London, England

[73] Assignee: Beecham Group Limited, England

[21] Appl. No.: 741,215

[22] Filed: Nov. 12, 1976

Related U.S. Application Data

[60] Continuation-in-part of Ser. No. 612,237, Sep. 11, 1975, abandoned, which is a continuation of Ser. No. 444,791, Feb. 22, 1974, abandoned, which is a division of Ser. No. 261,042, Jun. 8, 1972, abandoned.

[30] Foreign Application Priority Data

June 12, 1971 [GB] United Kindgom ............... 27653/71

[51] Int. Cl.$^3$ .......................................... C07D 309/10
[52] U.S. Cl. ............................................ 260/345.8 R
[58] Field of Search ...................... 260/345.8 R, 345.8

[56] References Cited

FOREIGN PATENT DOCUMENTS 2227739 1/1973 Fed. Rep. of Germany .

Primary Examiner—Norma S. Milestone
Attorney, Agent, or Firm—Jacobs & Jacobs

[57] ABSTRACT

An active antibacterial substance from *Pseudomonas fluoroescens* bacterium designated pseudominic acid and as a co-product a minor amount of a compound having an additional OH group designated as pseudomonic acid I. These two substances obtained are separated and purified. Alkali metal salts and methyl esters can be prepared. The antibacterial activity of pseudomonic acid appears to reside in the free acid form which results from in vivo hydrolysis of the methyl ester which is crystalline.

1 Claim, 3 Drawing Figures

ANTIBIOTICS

This application is a continuation-in-part of application Ser. No. 612,237, filed Sept. 11, 1975 now abandoned which is a continuation of application Ser. No. 444,791, filed Feb. 22, 1974, now abandoned, which in turn is a divisional of application Ser. No. 261,042, filed June 8, 1972, now abandoned.

This invention relates to an active antibiotic substance produced by the bacterium *Pseudomonas fluorescens*.

It has been known for many years that the bacterium *Pseudomonas fluorescens* produces inhibitory substances, and a convenient review of the published work on the subject can be found in the book "Antibiotics" by H. W. Florey, E. B. Chain, N. G. Heatley, M. A. Jennings, A. G. Saunders, E. P. Abraham, and M. E. Florey, published by the Oxford University Press (1949), Volume 1.

We have now succeeded in obtaining main and minor inhibitory substances which have been found to be essentially active pseudomonic acid with minor amounts of impurities.

The present invention therefore provides an antibiotic substance in substantially pure form designated as pseudomonic acid, having the formula (I):

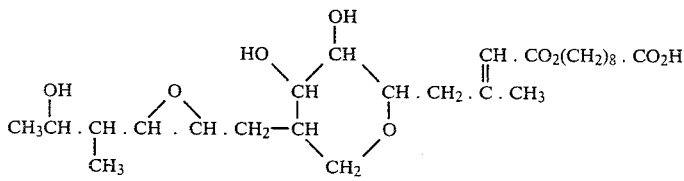

together with a minor amount of a closely related substance designated pseudomonic acid I having the formula (II):

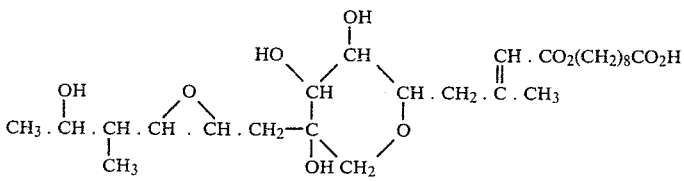

The methyl ester of the compound of formula (I) may readily be crystallized and recovered. We have named the compound of formula (I) "pseudomonic acid" and the compound of formula (II) "pseudomonic acid I", and they will be referred to as such hereinafter.

These compounds may be obtained and recovered together and then individually separated. Thus the present invention also provides, in substantially pure form, pseudomonic acid of formula (I) above, and the alkali metal salts and esters thereof, e.g. the sodium salts and methyl esters.

Figure 1B:
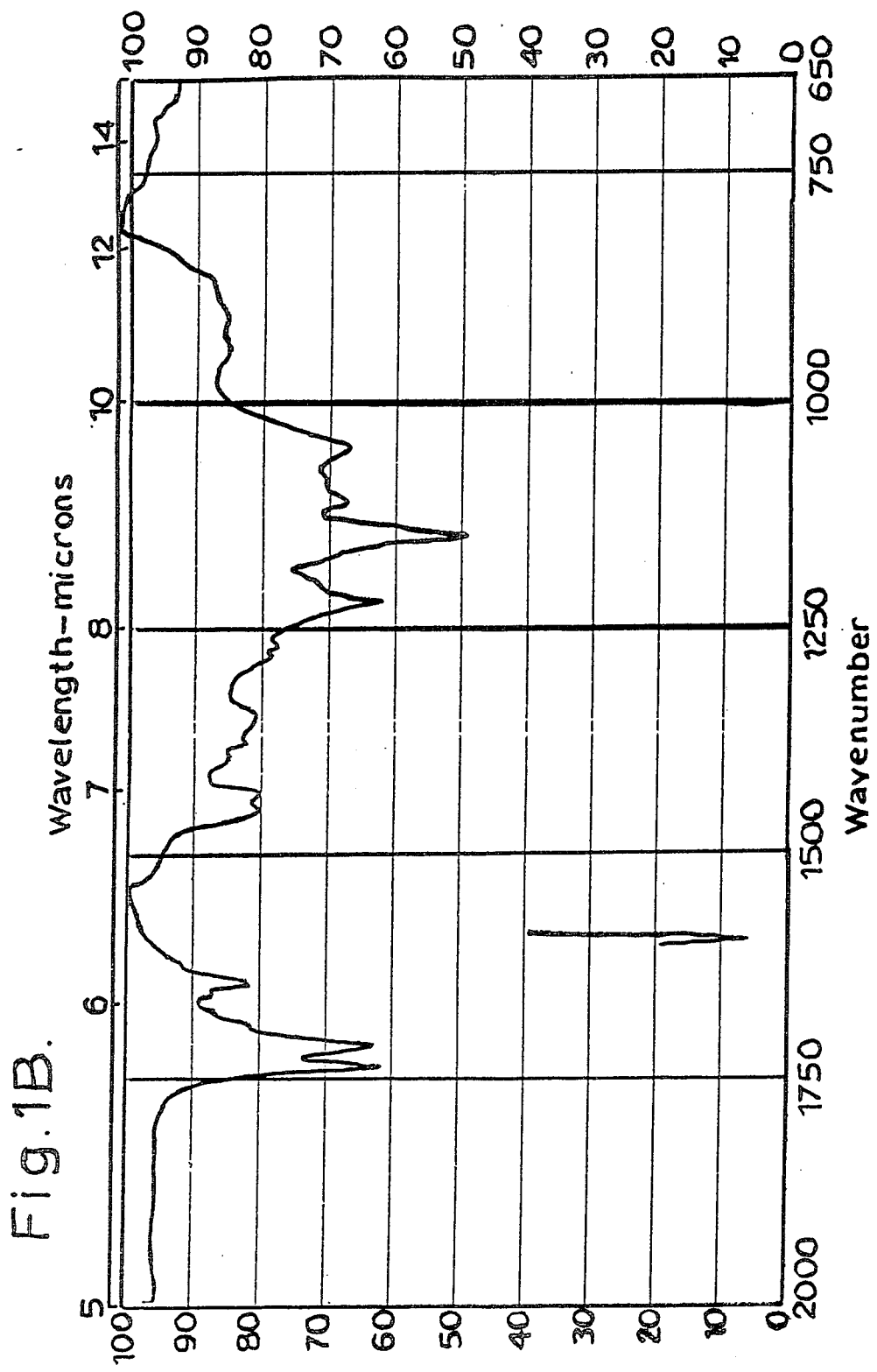
Figure 2:
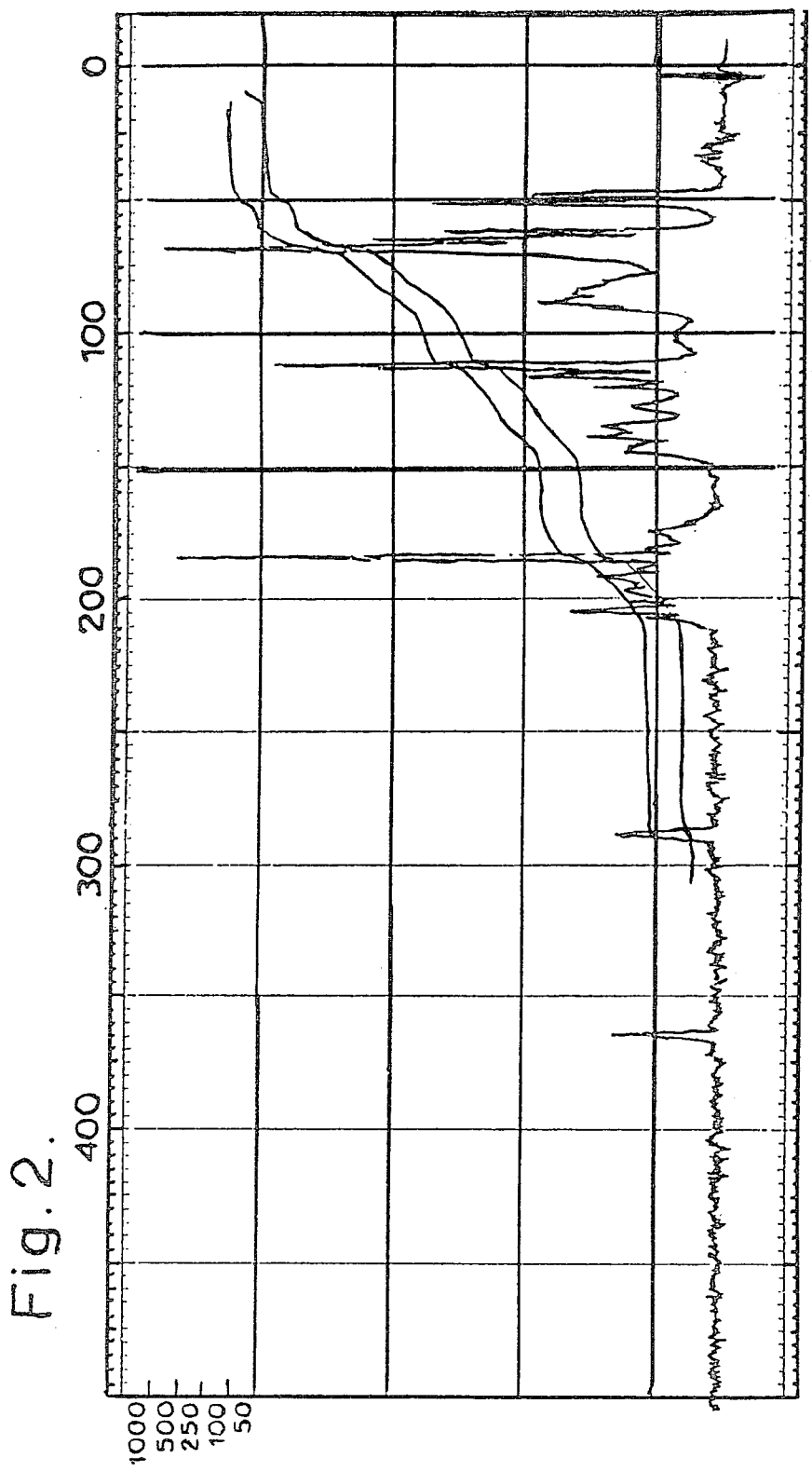

Pseudomonic acid is conveniently obtained and characterized in the form of its crystalline methyl ester, which has the infra-red spectrum shown in FIG. 1 of the accompanying drawings and the proton magnetic resonance spectrum shown in FIG. 2 of the accompanying drawings.

Pseudomonic acid of Formula (I) has antibacterial activity and its activity appears to be associated with the presence of the free carboxyl group. Thus the alkali metal salts of pseudomonic acid and the methyl and p-bromophenacyl esters of the carboxyl group —$CO_2H$ are also active while in the salt and ester form. Hence the present invention also provides the alkali metal salts of pseudomonic acid and other derivatives of the free carboxyl group which are readily hydrolyzed to give the parent active free pseudomonic acid.

It is believed from existing evidence that the compound represented by Formula (I) above exists as pseudomonic acid of trans-configuration at the double bond.

The present invention also provide in substantially pure form an amount of pseudomonic acid I of Formula (II) above and alkali metal salts and lower alkyl esters thereof.

Also included within the scope of the present invention is a process for the preparation and recovery of the compounds of Formula (I) and (II) in substantially pure form, which process comprises growing *Pseudomonas fluorescens* under aerobic conditions on or in a culture medium containing inorganic salts and sources of assimilable carbon and nitrogen until the culture medium exhibits at least detectable antibacterial activity, thereafter adding a source of barium ions to the culture medium and removing the resultant precipitated material therefrom, extracting the culture medium with an organic solvent for the active materials, dissolved in the culture medium, extracting the resultant organic solution with water at a pH between 7 and 9, evaporating the water to leave a solid residue. The active pseudomonic acid is recovered from the solid residue by recrystallization or other accepted purification procedure.

In the above-defined process, the cultivation step where *Pseudomonas fluorescens* is grown is conventional. All strains of this organism known to us produce pseudomonic acid to a greater or lesser extent, but one suitable public strain is *Pseudomonas fluorescens* N.C.I.B. 10586 (NCIB=National Collection of Industrial Bacteria).

However, we regard the next step, i.e. the addition of a source of barium ions to the culture medium, as being the step which enables practical separation of the components to be carried out efficiently. It appears that the major proportion of the active culture fluid is converted in this step to soluble barium salts (which in itself is surprising since most barium salts are water-insoluble) while the residual components which are primarily impurities are left behind as an insoluble precipitate.

After removal of the precipitate the active substance is extracted from the aqueous solution with a suitable extractant solvent. Suitable solvents can be determined by simple trial and error, but we find that isobutyl-methyl ketone (IBMK) is a good solvent. Other solvents include ether containing 5% ethanol, and also chloroform (although these two are not as efficient as IBMK).

The organic solution is then extracted with water at an alkaline pH and the salts of the active materials are obtained by evaporating the water. If desired, the extraction with organic solvent followed by alkali can be repeated several times to ensure efficient extraction and purification of active material.

The separation of inactive contaminations from the resulting salts can be achieved either by ion-exchange chromatography of the crude salts or by esterifying the salts at the carboxyl group —$CO_2H$ and subjecting the esterified mixture to silica gel chromatography. When using ion-exchange methods we find that a polystyrene resin column eluted with a gradient of 0.01 N methanolic ammonia in 0.01 N aqueous ammonia is a suitable system. Using this system, a series of low molecular weight inactive acids are eluted first, followed by the active fraction (30%-60% elution).

In a further aspect, the present invention provides a process for the preparation of pseudomonic acid, in substantially pure form which process comprises producing the active substance as in the previous aspect of the invention, esterifying the same to produce lower alkyl esters, separating out the pseudomonic acid ester and de-esterifying said ester as by hydrolysis or enzymatic cleavage, thereby producing the antibiotically active pseudomonic acid.

In order to carry out the process aspect of this invention, the active substance is esterified, e.g. by conversion to the methyl ester, and the ester recovered. This may be achieved by thin layer chromatography in the conventional way, e.g. on silica gel developed by chloroform/isopropanol (9:1). This provides the ester of pseudomonic acid I, which is present in minor amount, and the antibiotically active main product pseudomonic acid methyl ester which can be recovered in crystallized form.

De-esterification, when desired, will vary somewhat according to the particular ester involved. With the p-bromophenacyl ester of the carboxylic acid group —$CO_2H$, the method of Sheehan et al. J. Org. Chem (1964), Vol. 29, p. 2006 may be employed (i.e. treatment with sodium thiophenoxide).

The invention is illustrated by the following examples:

EXAMPLE 1

Production and recovery of Antibacterially active pseudomonic acid and Pseudomonic acid (I)

*Pseudomonas fluorescens*, strain NCIB. 10586 was grown in submerged culture at 30° C. in a medium containing 1% corn steep liquor and 0.5% glucose in a basic salts solution. The maximum yield of the antibiotic occurred after 24 hours and all of the detectable activity was in the culture fluid. After the addition of barium chloride (0.5%) the cells and precipitated non-active contaminant material were removed by centrifugation. The activity was progressively concentrated by partitioning into isobutylmethyl ketone (IBMK) (0.2 vol) at pH 4.5 water (0.8 vol) at pH 8.5, and then IBMK (0.25 vol) at pH 4.5 followed by evaporation to a small volume under reduced pressure. After a further partition into water at pH 8.5 and then adjustment to pH 7-8 the aqueous solution was freeze dried to give the sodium salt which could be stored at 0° C. for several months, without loss of activity.

The antibiotic extract was stable within the range pH 4-9 at 37° C. for 24 hours. Outside these limits rapid loss of activity occurred. The sodium salt showed a broad antibacterial spectrum against Gram positive and Gram negative bacteria, showed low toxicity and was bacteriostatic against *S. aureus* (N.C.T.C. 6571) and *E. coli* (M.R.E. 600).

Further purification of the crude acid was effected by chromatography on Amberlite XAD-2 polystyrene resin with a linear gradient produced by adding 0.1 N methanolic ammonia, to 0.01 N aqueous ammonia. A series of low molecular weight acids was eluted first, followed by a fraction (30-60% elution) that possessed the major part of the antibacterial (biological) activity.

EXAMPLE 2

Purification of Pseudomonic acid and Pseudomonic Acid I

The biologically active material produced in Example 1 upon methylation with diazomethane in ether showed two spots by thin layer chromatography corresponding to methyl pseudomonate as the major component and a minor amount of component methyl pseudomonate-I (ratio ca 9:1 by wt.).

Methyl pseudomonate (ca 9 parts by wt.) was separated from methyl pseudomonate-I (ca. 1 part by wt.) by preparative layer silica gel ($GF_{245}$) chromatography on development with chloroform/isopropanol (9:1). 50% by wt. of methyl pseudomonate was recovered from the impure residue by crystallization from benzene/petroleum ether to give colorless needles of m.p. 76.5°-78°.

Elemental analysis indicated the formula $C_{27}H_{46}O_9$ (Found: C, 6.28; H, 8.9. $C_{27}H_{46}O_9$ required C, 63.0; H, 9.0%), and the ester is optically active ($[\alpha]_D^{24} -9°$) (C, 1.5 in chloroform). Analysis of the oily p-bromophenacyl ester indicated a formula $C_{34}H_{49}BrO_{10}$ (Found: C, 58.1; H, 6.9 $C_{34}H_{49}BrO_{10}$ requires C, 58.5; H, 7.0%). Hence the formula of the parent monocarboxylic acid, pseudomonic acid, is $C_{26}H_{44}O_9$. Further support for this derived from the mass spectrum of the methyl ester which showed the expected molecular ion at m/e 514. The infra-red spectrum of the methyl ester (FIG. 1) showed $\nu$max. ($CCl_4$) 3440 (hydroxyl), 1740 (ester), 1715 and 1650 $cm^{-1}$ ($\alpha,\beta$-unsaturated ester). The u.v. spectrum ($\lambda$max (EtOH) 221.5 nm ($\epsilon$13,400) confirms the presence of the $\alpha,\beta$-unsaturated ester linkage. The NMR spectrum (FIG. 2) showed the presence of two secondary methyl groups ($\gamma$9.09, 8.81), an olefinic methyl group ($\gamma$6.40) and an olefinic proton ($\gamma$4.32).

Acetylation of the methyl ester with pyridine/acetic anhydride affords a triacetate $C_{33}H_{52}O_{12}$, which absorbs 1 mole of hydrogen giving a dihydro derivative $C_{33}H_{54}O_{12}$ on catalytic hydrogenation. Reduction of the methyl ester with $LiAlH_4$ in tetrahydrofuran afforded 1,9-dihydroxynonanoate m.p. 46° (bis-phenylcarbamate derivative m.p. 168°-9°). Treatment of the p-bromophenacyl ester with $KMnO_4NaIO_4$ gave p-bromophenacyl-9-hydroxynonanoate, $C_{17}H_{23}BrO_4$, m.p. 77.5°-78° (Found: C, 55.1; H, 6.4. $C_{12}H_{23}BrO_4$ requires C, 55.0; H, 6.2%). Mild base hydrolysis of the methyl ester yielded methyl 9-hydroxynonanoate (iol) $C_{10}H_{20}O_3$. Further confirmation of the presence of the 9-hydroxynonanoate unit in pseudomonic acid is provided by the mass spectrum of the methyl ester. Mass measurement of the fragment at m/e 327 gave 327.18059 ($C_{17}H_{27}O_6$ requires 327.18059 corresponding to the loss of $-O(CH_2)_8CO_2CH_3$ from the molecular ion.

EXAMPLE 3

The following is a summary of further observations which lead us to postulate structures for pseudomonic acid and pseudomonic acid I.

(a) The presence of the $C_9$ unit in pseudomonic acid is confirmed by the reactions described in Example 2.

(b)
  (i) Attachment of $C_9$ unit to the rest of molecule.
  That the $C_9$ unit is attached to the rest of the molecule through an α,β-unsaturated ester linkage to which is attached a $-CH_3$ group (n.m.r chemical shift in methyl pseudomonate and certain derivatives) was proved by the following observations:
  Treatment of a hydroxyl protected derivative of methyl pseudomonate with (a) osmium tetroxide in pyridine, (b) aqueous sodium metabisulphate and (c) sodium periodate in aqueous ethanol gave a compound of formula:

$OCH.CO_2CH_2(CH_2)_6CH_2CO_2CH_3$ (characterized by analysis, nuclear magnetic resonance, and infra-red spectra; semi-carbazone derivative m.p 164°–165.6°) and also a nucleus methyl ketone derivative. This also proves that the $-CH_3$ group is attached to the β-carbon of the α,β-unsaturated ester system.
  (ii) Confirmation of double bond
  Methyl pseudomonate and its triacetate derivative absorb 1 mole hydrogen giving the respective dihydro derivatives, on catalytic hydrogenation showing only end absorption in the ultra-violet spectrum.
  (iii) Stereochemistry around double bond
  That the double bond was trans aligned was derived from the literature values of chemical shifts (nuclear magnetic resonance) of cis and trans $CH_3$ groups attached to double bonds of this type.

(c) Nature of functionalities in rest of molecule
  (a) Proof of Glycol system
    (i) Methyl pseudomonate forms an acetonide derivative, characterized by analysis, nuclear magnetic resonance, infra-red and ultraviolet spectra.
    (ii) Treatment of methyl pseudomonate with sodium periodate in aqueous ethanol gave a dialdehyde as sole product. Hence a glycol system is present and must be in a ring.
    (iii) This was also confirmed by n.m.r. double resonance experiments on the triacetate and tribenzoate derivatives,
  (b) Proof of epoxide
    (i) The presence of the epoxide was inferred from chemical shifts, in the n.m.r. spectra of methyl pseudomonate and derivatives, of the two attached protons. This was confirmed by n.m.r. double resonance and indor experiments.
  (c) Part structure $$\begin{array}{c} OH \\ | \\ (CH_3CH.CH.-) \\ | \\ CH_3 \end{array}$$

was inferred from the chemical shifts of the relevant protons (n.m.r.) in methyl pseudomonate acetonide derivative and the oxidation product, methyl pseudomonate acetoxide ketone derivative, with part structure $$\begin{array}{c} O \\ \| \\ (CH_3.C.CH-) \\ | \\ CH_3 \end{array}$$

(D) Using indor and double resonance techniques in the n.m.r. specta of the nucleus methyl ketone triacetate and tribenzoate derivatives, the structure of the nucleus methyl ketone was deduced and hence the structure of pseudomonic acid shown to be as formula (I) herein.

PSEUDOMONIC ACID I

The spectra of methyl pseudomonate I and its triacetate derivative (mass spectrum, ultra-violet, n.m.r. and infra-red) indicated its close relationship to methyl pseudomonate and that it possessed an additional hydroxyl group.

The structure shown in formula (II) herein was deduced from n.m.r. double resonance experiments on the triacetate derivative of the nucleus methyl ketone.

EXAMPLE 4

Hydrolysis of p-bromophenacyl ester of impure pseudomonic acid

To the p-bromophenacyl ester (234 mg) in dimethyl formamide (3 ml) was added sodium thiophenoxide (230 mg). After 30 min, excess ice-cold acetone was added and the reaction mixture kept 2 hr at 20°. The impure sodium salt of the pseudomonic acid collected by centrifugation. The sodium salt was dissolved in water and the pH adjusted to pH 4.5 with dil. HCl. The free acid was extracted into ether containing 5% EtOH. The ethereal layer was washed with water, dried and evaporated to 15 ml in vacuo to give the impure free acid.

Esterification of acid

To the above impure acid an excess of ethereal diazomethane was added. After 1 hr the solvent was removed in vacuo and the product was purified by preparative layer chromatography on Kieselgel $GF_{254}$ developing twice with 3% isopropanol in chloroform. Band $R_F$ 0.2–0.25 afforded the impure methyl ester of pseudomonic acid as an oil (180.3 mg), νmax ($CHCl_3$) 3440 br. 1735, 1710, 1220, 1155, 1050 $cm^{-1}$: λmax (EtOH) 220 nm (ε1600); τ9.09 3H, d (J 7 HZ); τ8.81 3H, d (J6.5 HZ); τ7.84, 3H, d (J 1 HZ) and τ4.32, 1 H br.s.

The above methyl ester was identical (t.l.c., u.v., I.R. and N.M.R.) with the impure methyl ester prepared directly from the acidic extract of the fermentation culture fluid by treatment with ethereal diazomethane.

EXAMPLE 5

Procedure for salt formation

This is typified by the formation of the sodium salt of pseudomonic acid as obtained following purification on the XAD-2 resin. The impure acid was dissolved in isobutyl methyl ketone and extracted into water by the gradual addition of dilute aqueous sodium hydroxide until the pH of the aqueous layer reached 7. The aqueous layer was lyophilized to give the sodium salt of the impure acid. The barium salt was similarly obtained.

What is claimed is:

1. The methyl ester of pseudomonic acid I having the formula:

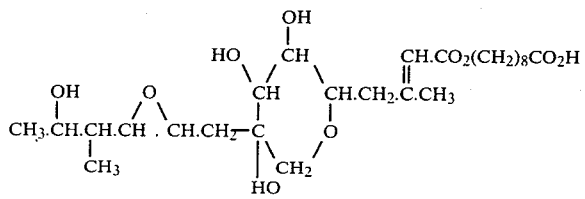

and being in substantially pure form.

* * * * *